United States Patent
Runge et al.

(10) Patent No.: US 6,235,315 B1
(45) Date of Patent: May 22, 2001

(54) STABLE, PULVERULENT LYCOPENE FORMULATIONS, COMPRISING LYCOPENE HAVING A DEGREE OF CRYSTALLINITY OF GREATER THAN 20%

(75) Inventors: Frank Runge, Maxdorf; Helmut Auweter, Limburgerhof, both of (DE); Nina Musaeus-Jensen, Hellerup (DK); Herbert Haberkorn, Grünstadt; Jens Rieger, Ludwigshafen, both of (DE)

(73) Assignee: BASF Aktiengesellschaft, Ludwigshafen ( * ) Notice: Subject to any disclaimer, the term of this patent is extended or adjusted under 35 U.S.C. 154(b) by 0 days.

(21) Appl. No.: 09/395,772

(22) Filed: Sep. 14, 1999

(30) Foreign Application Priority Data

Sep. 14, 1998 (DE) .................................. 198 41 930

(51) Int. Cl.[7] .............................. A61K 9/72; A61K 9/14; A61K 47/00
(52) U.S. Cl. ........................ 424/489; 424/40; 424/438; 424/437; 424/442
(58) Field of Search ............................ 424/489, 40, 438, 424/439, 442; 426/311, 801; 264/4.1, 5

(56) References Cited

U.S. PATENT DOCUMENTS

| | | | |
|---|---|---|---|
| 4,182,731 | 1/1980 | Schulz et al. ................. | 260/606 |
| 4,522,743 | 6/1985 | Horn et al. ..................... | 252/311 |
| 5,166,445 | 11/1992 | Meyer ............................. | 568/2 |
| 5,208,381 | 5/1993 | Meyer ............................. | 568/10 |
| 5,364,563 | 11/1994 | Cathrein et al. ............... | 252/311 |

FOREIGN PATENT DOCUMENTS

| | | |
|---|---|---|
| 2214480 | 3/1998 | (CA) . |
| 1211911 | 8/1960 | (DE) . |
| 000140 | 1/1979 | (EP) . |
| 065193 | 11/1982 | (EP) . |
| 382067 | 8/1990 | (EP) . |
| 410236 | 1/1991 | (EP) . |
| 832569 | 4/1998 | (EP) . |
| 91/06292 | 5/1991 | (WO) . |
| 94/19411 | 9/1994 | (WO) . |
| 97/48287 | 12/1997 | (WO) . |
| 98/16204 | 4/1998 | (WO) . |

OTHER PUBLICATIONS

Manz et al., *Chimia* 21, 1967, pp. 329–335.

*Primary Examiner*—Thurman K. Page
*Assistant Examiner*—Amy Pulliam
(74) *Attorney, Agent, or Firm*—Keil & Weinkauf

(57) ABSTRACT

The invention relates to stable, pulverulent lycopene formulations, comprising lycopene having a degree of crystallinity of greater than 20%, processes for their preparation and their use as an additive to foodstuffs, cosmetics, pharmaceuticals and animal feedstuffs.

11 Claims, 1 Drawing Sheet

Figure 1:
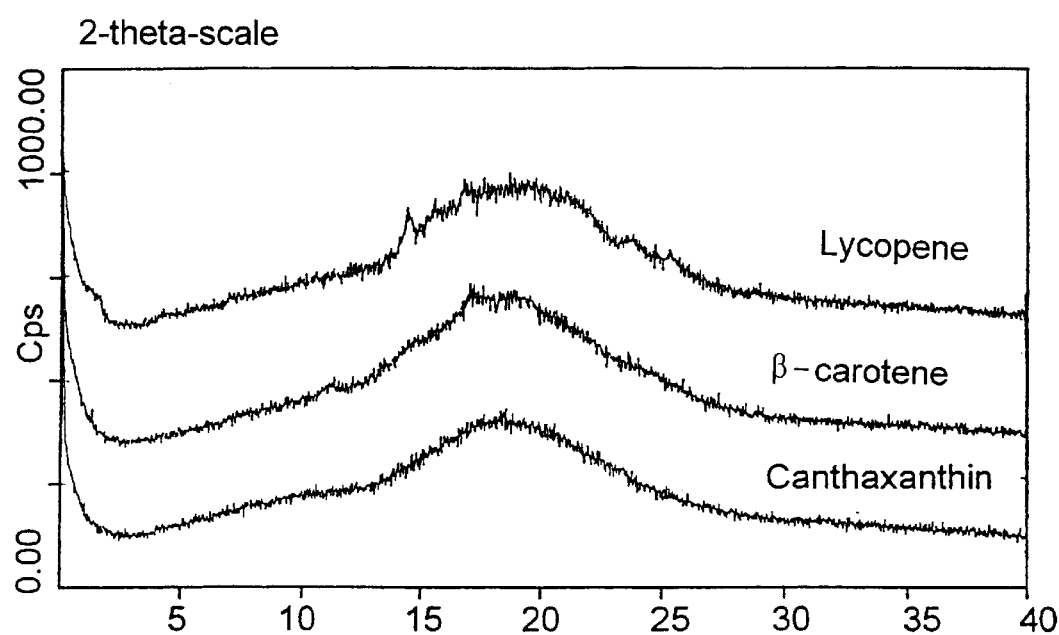

STABLE, PULVERULENT LYCOPENE FORMULATIONS, COMPRISING LYCOPENE HAVING A DEGREE OF CRYSTALLINITY OF GREATER THAN 20%

Stable, pulverulent lycopene formulations, comprising lycopene having a degree of crystallinity of greater than 20%.

The invention relates to stable, pulverulent lycopene formulations, comprising lycopene having a degree of crystallinity of greater than 20%, processes for their preparation and their use as an additive to foodstuffs, cosmetics, pharmaceuticals and animal feedstuffs.

Lycopene, which belongs to the carotenoids class of substances, occurs widely in nature. Thus tomatoes having a lycopene content of about 20 mg/kg of tomato form the most important natural source of this red pigment.

Epidemiological studies have shown that a more frequent and regular consumption of tomatoes or tomato products decreases the risk of chronic disorders, inter alia cardiac and circulatory disorders, and exerts a positive effect on the prevention of cancer. This protective function of lycopene is seen in its action as a very effective antioxidant.

Both for the foodstuffs and feedstuffs industry and for pharmaceutical technology, lycopene, for example as a substitute for artificial colorants, represents an important coloring material and is moreover of interest for the reasons mentioned at the outset as a foodstuff additive for healthcare.

The synthesis of lycopene is described, inter alia, in EP-A-382067 and EP-A-000140. WO 97/48287 describes the extraction of lycopene as a natural carotenoid from tomatoes.

Like all carotenoids, lycopene is also insoluble in water, while in fats and oils a solubility which, however, is only slight is found. This limited solubility and the high sensitivity to oxidation stand in the way of direct use of the relatively coarse-grain crystalline lycopene in the coloration of foodstuffs and feedstuffs, since the pure substance is too unstable in coarse-crystalline form, is only inadequately absorbed and thus yields only poor coloring results.

Only by means of specifically prepared formulations in which the active compounds are present in finely divided form, and if appropriate protected against oxidation by protective colloids, can improved color yields be achieved in the direct coloring of foodstuffs.

In view of the particularly low stability to oxidation, in comparison with other carotenoids, and the low color stability and storage stability of lycopene also connected therewith, particularly high demands are placed on these formulations.

For carotenoids generally, a large number of formulations and processes for their preparation are described.

Thus lycopene, for example, is obtainable under the name Lyc-O-Mato® (LycoRed, Israel) as a 6% strength oily dispersion. It is extracted from tomatoes as a natural carotenoid according to WO 97/48287. On account of the high phospholipid content in the Lyco-O-Mato®, combined with a high viscosity of the oily dispersion, the application properties of this formulation, inter alia the water dispersibility, are not satisfactory.

EP-A-0 410 236 describes a process for the preparation of carotenoid dry powders, in which a suspension of a carotenoid is briefly heated in a high-boiling oil, this mixture of molten carotenoid and oil is emulsified in an aqueous solution of a colloid and this emulsion is then spray dried.

DE-A-1 211 911, describes carotenoid products for whose preparation firstly the carotenoids are dissolved in a water-insoluble solvent, and then this solution is emulsified into an aqueous protective colloid solution and spray dried.

EP-A-0 065 193 describes a process for the preparation of pulverulent carotenoid products, which comprises briefly dissolving a carotenoid in a water-miscible, organic solvent at elevated temperatures, immediately precipitating the carotenoid in colloidally disperse form from the resulting solution by rapid mixing with an aqueous solution of a protective colloid and converting the resulting dispersion into a dry powder.

According to EP-A-0 832 569, a carotenoid dry powder in which the active compound particles are largely present in X-ray amorphous form is obtained by heat treatment of the dispersion prepared according to EP-A-0 065 193 at a temperature between 40° C. and 90° C. and subsequent spray drying.

WO 98/16204 describes a process for the preparation of pulverulent carotenoid products, which comprises dissolving a carotenoid in dimethyl ether in an autoclave at elevated pressure and temperature and removing the solvent again by very rapid depressurization.

Numerous methods, described, inter alia, in Chimia 21, 329 (1967), WO 91/06292 and in WO 94/19411, make use of the grinding of carotenoids, e.g. β-carotene, by means of a colloid mill, and thus achieve particle sizes of 2 to 10 μm.

Despite the large number of publications in this area, information for solving the stability problem of lycopene going beyond general statements about carotenoid formulations is found in none of the texts mentioned in the prior art.

It is therefore an object of the present invention to make available pulverulent lycopene formulations in which the lycopene is particularly stable to oxidation and light and which do not have the above mentioned disadvantage of the prior art.

We have found that this object is achieved according to the invention by stable, pulverulent lycopene formulations comprising lycopene having a degree of crystallinity of greater than 20%.

The degree of crystallinity of lycopene in the formulations according to the invention can be determined, for example, by X-ray diffraction measurements and in general lies in the range greater than 20%, preferably in the range from 25 to 100%, particularly preferably in the range from 30 to 95%, very particularly preferably in the range from 40 to 80%.

With respect to double bond isomerism, the lycopene contained in the pulverulent formulations can be present without restriction in all isomeric forms, for example in the all-trans, 5-cis or 9,13-di-cis form. Preferred pulverulent formulations are those comprising lycopene having an all-trans content of at least 50%, particularly preferably lycopene having an all-trans content of 52 to 100%, very particularly preferably lycopene having an all-trans content of 55 to 90%.

The content of lycopene in the formulations according to the invention lies in the range from 0.5 to 25% by weight, preferably in the range from 2 to 21% by weight, particularly preferably in the range from 5 to 16% by weight, very particularly preferably in the range from 8 to 12% by weight, based on the dry mass of the formulations.

The mean particle size of lycopene in the dry powders lies in the range below 10 μm, preferably in the range below 5.0 μm, particularly preferably in the range from 0.05 to 1 μm.

To increase the stability of the pulverulent lycopene formulations, it is advantageous to incorporate into the formulation protective colloids, plasticizers and/or stabilizers, additionally to the active compound.

Protective colloids used are, for example, gelatin, fish gelatin, starch, dextrin, plant proteins, pectin, gum arabic, casein, caseinate or mixtures thereof. However, polyvinyl alcohol, polyvinylpyrrolidone, methylcellulose, carboxymethylcellulose, hydroxypropylcellulose and alginates can also be employed. For more details, reference is made to R. A. Morton, Fat Soluble Vitamins, Intern. Encyclopedia of Food and Nutrition, Vol. 9, Pergamon Press 1970, pp. 128–131. To increase the mechanical stability of the final product, it is expedient to add a plasticizer, such as sugars or sugar alcohols, e.g. sucrose, glucose, lactose, invert sugar, sorbitol, mannitol or glycerol, to the colloid.

The ratio of protective colloid and plasticizer to carotenoid solution is in general selected such that a final product is obtained which contains between 0.5 and 25% by weight of lycopene, 10 to 50% by weight, preferably 15 to 35% by weight, of a protective colloid, 20 to 70% by weight, preferably 30 to 60% by weight, of a plasticizer, all percentage data based on the dry mass of the powder, and, if appropriate, minor amounts of a stabilizer.

To increase the stability of the active compound against oxidative degradation, it may be advantageous to add 0 to 10% by weight, preferably 0.5 to 7.5% by weight, based on the dry matter of the formulation, of one or more stabilizers such as α-tocopherol, t-butylhydroxytoluene, t-butylhydroxyanisole, ascorbic acid or ethoxyquin.

Furthermore, it is possible to use emulsifiers, for example ascorbyl palmitate, polyglycerol fatty acid esters, sorbitan fatty acid esters, propylene glycol fatty acid esters or lecithin in a concentration of 0 to 200% by weight, preferably 5 to 150% by weight, particularly preferably 10 to 80% by weight, based on lycopene.

Under certain circumstances, it can also be advantageous to additionally use a physiologically approved oil such as, for example, sesame oil, corn oil, cottonseed oil, soybean oil or peanut oil and esters of medium chain vegetable fatty acids in a concentration of 0 to 500% by weight, preferably 10 to 300% by weight, particularly preferably 20 to 100% by weight, based on lycopene.

In addition to lycopene, the formulations can also contain further carotenoids, such as, for example β-carotene, bixin, zeaxanthin, cryptoxanthin, citranaxanthin, canthaxanthin, β-apo-4-carotenal, β-apo-8-carotenal, β-apo-8-carotenoic acid esters, astaxanthin or lutein, individually or as a mixture.

The invention also relates to a process for the preparation of the stable, pulverulent lycopene formulations described at the outset, comprising lycopene having a degree of crystallinity of greater than 20%, which comprises a) preparing a molecularly disperse solution of lycopene, if appropriate together with an emulsifier and/or an edible oil, in a water-miscible, organic solvent or a mixture of water and a water-miscible, organic solvent at temperatures greater than 30° C., b) mixing this solution with an aqueous solution of a protective colloid, the hydrophilic solvent component being transferred into the aqueous phase, and the hydrophobic phase of the carotenoid resulting as a nanodisperse phase, c) and freeing the formed dispersion from the solvent and the water for the preparation of a water-dispersible dry powder and, if appropriate, drying in the presence of a coating material.

Especially suitable for carrying out the process according to the invention are water-miscible, thermally stable, volatile solvents containing only carbon, hydrogen and oxygen, such as alcohols, ethers, esters, ketones and acetals. Preferably, ethanol, n-propanol, isopropanol, 1,2-butanediol 1-methyl ether, 1,2-propanediol 1-n-propyl ether or acetone is used. Generally, the solvents expediently used are those which are at least 10% water-miscible, have a boiling point of below 200° C. and/or have less than 10 carbons.

In a preferred embodiment of the process, in step a) the molecularly disperse lycopene solution is prepared at temperatures from 50° C. to 240° C., particularly preferably at temperatures from 140° C. to 180° C., and immediately subsequently mixed with the aqueous solution of the protective colloid in step b), a mixing temperature of approximately 35° C. to 80° C., particularly preferably from 55° C. to 70° C., being set.

Since the action of high temperatures can reduce the desired high all-trans isomer content, the lycopene is dissolved as rapidly as possible, for example in the seconds range, e.g. in 0.1 to 10 seconds, particularly preferably in less than 1 second. For the rapid preparation of the molecularly disperse solution, the use of elevated pressure, e.g. in the range from 20 bar to 100 bar, preferably 30 to 80 bar, may be advantageous.

Depending on the type and amount of protective colloid used, a deep-colored viscous liquid is obtained by process step b). The removal of the solvent can be carried out, for example, by extraction with a water-immiscible solvent or, depending on the boiling point, in a manner known per se, e.g. by distillation, if appropriate under reduced pressure. In this case, it has proven expedient and possible to employ as solvent the azeotrope obtained on use of isopropanol directly, without removal of water. Preferably, the solvent removal is carried out, however, together with the removal of the water by spray drying or spray granulation.

For a more detailed description of the process and apparatus, reference is expressly made here to EP-A-0 065 193.

The lycopene dry powders prepared by the above process are distinguished by a very good redispersibility, both in warm and in cold water.

It has now been found that a pulverulent lycopene formulation prepared by the abovementioned process has surprising properties in comparison with corresponding β-carotene or canthaxanthin formulations. While β-carotene and canthaxanthin are present in mainly amorphous form with a degree of crystallinity of only 10% in a dry powder prepared according to EP-A-0 065 193, the degree of crystallinity of lycopene in the preparation, determined with the aid of X-ray diffraction diagrams, shows values in the range greater than 20%, preferably in the range from 25 to 100%, particularly preferably in the range from 30 to 95%, very particularly preferably in the range from 40 to 80%.

FIG. 1 depicts the respective X-ray diffraction diagrams of the dry powders of lycopene, β-carotene and canthaxanthin described in Table 1. The wide-angle X-ray diagrams were recorded in the angular range $1°≦2\theta≦40°$. The determination of the active compound crystallinity $W_{cw}$ was carried out in the diagram section $11°≦2\theta≦31°$, in which the majority of the active compound interference occurs, according to the formula $W_{cw}=F_{cw}/F_{100}·c_w$. $F_{100}$ in this case is the crystalline scattering of the pure active compound measured under comparable conditions and found by planimetry in the same angular range and $c_w$ is the concentration of the active compound in the formulation.

It was also surprising that the lycopene formulations according to the invention prepared in this way are distinguished by a particular light stability in the photochemical stability test in comparison with corresponding β-carotene and canthaxanthin formulations (see Table 1).

TABLE 1

| Dry powder of:[1] | Content [% by weight] | All-trans content [%] | Degree of crystallinity [%] | Half-life[2] [min] |
|---|---|---|---|---|
| Lycopene | 10 | 72 | 64 | 160 |
| β-carotene | 10 | 78 | 10 | 28 |
| Canthaxanthin | 10 | 73 | 0 | 34 |

[1] Prepared according to Example 1
[2] Irradiation time after which the initial extinction at the absorption maximum has decreased to one half in the light stability test[3].
[3] In the light stability test, the dry powder to be investigated in each case was dispersed in demineralized water, adjusted to pH 3 using citric acid and irradiated in a Suntest CPS apparatus (Heraeus) in 50 ml quartz ampoules with access to air. The UV/VIS spectrum was measured as a function of the irradiation time.

The invention moreover relates to a further process for the preparation of stable, pulverulent lycopene formulations, comprising lycopene having a degree of crystallinity of greater than 20%, which comprises grinding crystalline lycopene having an all-trans isomer content of at least 50% in an aqueous medium in the presence of a protective colloid and drying the lycopene suspension thus obtained for the preparation of a dry powder. The dry powder thus obtained can in turn be readily redispersed in water, for example for coloring purposes.

For a more detailed description of the process and apparatus, reference may be made here expressly to EP-A-0 498 824.

Surprisingly, in the grinding process claimed above for the preparation of lycopene dry powders, it was possible to adjust the degree of crystallinity of lycopene by variation of the grinding time and/or grinding temperature.

In addition to the advantageous color stabilities of the lycopene dry powders according to the invention already mentioned, very good storage stabilities were also observed. Thus a lycopene-containing formulation prepared by the grinding process, for example, shows an outstanding storage stability in pharmaceutical products, for example in multivitamin tablets (see Table 2).

TABLE 2

| Dry powder of:[1] | Content [% by weight] | Degree of crystallinity [%] | Content after a storage time of 3 months[2] [%] |
|---|---|---|---|
| Lycopene | 10 | 33 | 89 |
| Lycopene | 10 | 25 | 80 |
| Lycopene | 10 | 19 | 60 |

[1] Prepared according to Example 3
[2] Storage stability of lycopene in multivitamin/mineral tablets, storage at 40° C. and 75% atmospheric humidity In addition to the processes according to the invention for the preparation of the lycopene formulation, other preparation processes, inter alia those cited at the outset as prior art, are is optionally also conceivable, for example a combined emulsification and spray-drying process.

The invention also relates to stable, aqueous lycopene dispersions, comprising lycopene having a degree of crystallinity of greater than 20%.

These dispersions are obtained, for example, by dispensing with the drying step, e.g. the spray drying, in the process for the preparation of the lycopene dry powder according to the invention.

Just like the pulverulent lycopene formulations, the aqueous lycopene dispersions exhibit a very good light stability.

The lycopene formulations according to the invention are suitable, inter alia, as an additive for foodstuff preparations, as compositions for the production of pharmaceutical and cosmetic preparations and for the production of food supplement products in the human and veterinary sector.

Typical areas of use in the foodstuffs sector are, for example, the coloration of drinks, milk products such as yogurts, milk drinks or milk-based ice cream and of blancmange powders, egg products, baking mixtures and confectionery.

In the foodstuffs sector, the lycopene formulations can be used, for example, for egg yolk and broiler skin pigmentation in poultry rearing.

In the cosmetics sector, the lycopene dry powders can be used, for example, as colorants for decorative body care compositions.

The invention also relates to food supplements, animal feedstuffs, foodstuffs and pharmaceutical and cosmetic preparations comprising the lycopene formulations described above.

Food supplement products and pharmaceutical preparations which contain the lycopene formulation according to the invention are to be understood as meaning, inter alia, tablets, coated tablets and hard and soft gelatin capsules.

Cosmetic preparations which can contain the lycopene formulations according to the invention are, for example, topically applicable preparations, in particular decorative body care compositions such as lipsticks, face make-up in the form of a cream, a lotion, a powder or alternatively as rouge.

The preparation of the lycopene formulations according to the invention is explained in greater detail in the following examples.

EXAMPLE 1

Preparation of a 10% Strength Lycopene Dry Powder 25 g of cryst. lycopene were suspended in a solution of 4.6 g of ascorbyl palmitate and 3.6 g of α-tocopherol in 300 g of isopropanol. This suspension was mixed with 400 g of isopropanol (feed rate 2.6 kg/h), which was heated by means of a heat exchanger, at a feed rate of 2.0 kg/h and a system pressure of 50 bar. The molecularly disperse solution formed in the course of this at a temperature of 170° C. was turbulently mixed in a mixing chamber with a solution of 72.4 g of fish gelatin and 108 g of glucose syrup in 4776 g of water delivered at 30.5 kg/h to form a dispersion of a microdisperse lycopene phase in a water/isopropanol mixture (lycopene content 0.3%). The dispersion was concentrated in a vacuum evaporator (lycopene content 3.0%), the isopropanol being removed, and then converted into a dry powder by means of spray drying. The photometrically determined content of lycopene was 9.8%.

The mean particle size determined by quasi-elastic light scattering was 134 nm. The all-trans content determined by HPLC was 72%; the degree of crystallinity of the lycopene determined by means of wide-angle X-ray scattering was 64%.

EXAMPLE 2

Preparation of a 20% Strength Lycopene Dry Powder 50 g of cryst. lycopene were suspended in a solution of 4.6 g of ascorbyl palmitate and 3.6 g of α-tocopherol in 275 g of isopropanol. This suspension was mixed with 433 g of isopropanol (feed rate 2.6 kg/h), which was heated by means of a heat exchanger, at a feed rate of 2.0 kg/h at a system pressure of 50 bar. The molecularly disperse solution formed in the course of this at a temperature of 170° C. was turbulently mixed in a mixing chamber with a solution of 72.4 g of fish gelatin and 108 g of glucose syrup in 4773 g of water delivered at 30.5 kg/h to form a dispersion of a microdisperse lycopene phase in a water/isopropanol mixture. The dispersion was concentrated in a vacuum evaporator (lycopene content 4.8%) and then converted into a dry powder by means of spray drying. the photometrically determined content of lycopene was 20%.

The mean particle size determined by quasi-elastic light scattering was 244 nm. The all-trans content determined by HPLC was 52%; the degree of crystallinity of the lycopene determined by means of wide-angle X-ray scattering was 51%.

EXAMPLE 3

Grinding of Crystalline Lycopene

Under protective gas, 15 g of crystalline lycopene were added to a solution, heated to 60° C., of 21 g of 240 Bloom A gelatin and 1.5 g of sodium ascorbate in 150 ml of water. The suspension was ground for 7 hours by means of a ball mill (DynoMill® Type KDL). After addition of 20 g of gelatin, 35 g of sucrose and 1.5 g of tocopherol, the suspension was spray dried. A dry powder having a lycopene content of 10% by weight was obtained. The all-trans content determined by HPLC was 91%; the degree of crystallinity of the lycopene determined by means of wide-angle X-ray scattering was 33%.

We claim:

1. A process for the preparation of stable, pulverulent lycopene formulations, comprising lycopene having a degree of crystallinity of greater than 20%, which comprises
    a) preparing a molecularly disperse solution of lycopene, if appropriate together with an emulsifier and/or an edible oil in a water-miscible, organic solvent or a mixture of water and a water-miscible, organic solvent at temperatures of greater than 30° C.,
    b) mixing this solution with an aqueous solution of a protective colloid, the hydrophilic solvent component being transferred into the aqueous phase, and the hydrophobic phase of the lycopene resulting as a nanodisperse phase,
    c) and freeing the formed dispersion from the solvent and the water for the preparation of a water-dispersible dry powder and, if appropriate, drying in the presence of a coating material.

2. A process as claimed in claim 1, wherein in step a) the molecularly disperse lycopene solution is prepared at temperatures from 50 to 240° C. and immediately subsequently mixed with the aqueous solution of the protective colloid in step b, a mixing temperature of approximately 35 to 80° C. being set.

3. A pulverulent lycopene formulation prepared by a process as claimed in claim 1, comprising lycopene having a degree of crystallinity of greater than 20%.

4. A lycopene formulation as claimed in claim 3, comprising 0.5 to 25% by weight of lycopene, 10 to 50% by weight of a protective colloid, 20 to 70% by weight of a plasticizer, 0 to 10% by weight of a stabilizer, all percentage data based on the dry mass of the powder.

5. A lycopene formulation as claimed in claim 3, comprising lycopene having an all-trans isomer content of at least 50%.

6. A lycopene formulation as claimed in claim 3, comprising lycopene having a particle size of less than 10 μm.

7. A lycopene formulation as claimed in claim 3, which is water-dispersible.

8. A process for the preparation of stable, aqueous lycopene dispersions, comprising lycopene having a degree of crystallinity of greater than 20%, which comprises
    a) preparing a molecularly disperse solution of lycopene, if appropriate together with an emulsifier and/or an edible oil in a water-miscible, organic solvent or a mixture of water and a water-miscible, organic solvent at temperatures of greater than 30° C.,
    b) mixing this solution with an aqueous solution of a protective colloid, the hydrophilic solvent component being transferred into the aqueous phase, and the hydrophobic phase of the lycopene resulting as a nanodisperse phase.

9. A stable, aqueous lycopene dispersion prepared by a process as claimed in claim 8, comprising lycopene having a degree of crystallinity of greater than 20%.

10. A food supplement, animal feedstuff, foodstuff or pharmaceutical or cosmetic preparation, comprising a lycopene formulation as defined in claim 3.

11. A food supplement, animal feedstuff, foodstuff or pharmaceutical or cosmetic preparation, comprising a lycopene dispersion as defined in claim 9.

* * * * *